United States Patent
Murray et al.

(10) Patent No.: US 11,172,844 B2
(45) Date of Patent: Nov. 16, 2021

(54) APPARATUS AND METHOD FOR DETECTION OF DYSFUNCTIONAL BREATHING

(71) Applicant: PMD Device Solutions Limited, Cork (IE)

(72) Inventors: Myles Murray, Cork (IE); Christopher Kinsella, Listowel (IE); Kevin Sweeney, Kilcloon (IE); Seán Kinsella, Carlow (IE)

(73) Assignee: PMD Device Solutions Limited, Cork (IE)

( * ) Notice: Subject to any disclaimer, the term of this patent is extended or adjusted under 35 U.S.C. 154(b) by 453 days.

(21) Appl. No.: 16/302,878

(22) PCT Filed: May 18, 2017

(86) PCT No.: PCT/EP2017/062032
§ 371 (c)(1),
(2) Date: Nov. 19, 2018

(87) PCT Pub. No.: WO2017/198787
PCT Pub. Date: Nov. 23, 2017

(65) Prior Publication Data
US 2019/0150787 A1    May 23, 2019

(30) Foreign Application Priority Data
May 19, 2016    (EP) .................................... 16170364

(51) Int. Cl.
*A61B 5/08*     (2006.01)
*A61B 5/113*    (2006.01)
*A61B 5/00*     (2006.01)

(52) U.S. Cl.
CPC .......... *A61B 5/0816* (2013.01); *A61B 5/1135* (2013.01); *A61B 5/6823* (2013.01); *A61B 2560/0412* (2013.01)

(58) Field of Classification Search
CPC ... A61B 5/0816; A61B 5/1135; A61B 5/6823; A61B 2560/0412
(Continued)

(56) References Cited

U.S. PATENT DOCUMENTS

| 6,935,335 B1 | 8/2005 | Lehrman et al. |
| 2011/0124979 A1 | 5/2011 | Heneghan et al. |

(Continued)

FOREIGN PATENT DOCUMENTS

| CN | 101569526 A | 11/2009 |
| GB | 2 396 012 A | 9/2004 |

(Continued)

OTHER PUBLICATIONS

International Search Report issued in PCT/EP2017/062032; dated Aug. 24, 2017.
(Continued)

*Primary Examiner* — David J. McCrosky
*Assistant Examiner* — Chanel J Jhin
(74) *Attorney, Agent, or Firm* — Renner, Otto, Boisselle & Sklar, LLP

(57) ABSTRACT

A monitoring method is performed by a digital processor while a subject is asleep or with little movement. The method includes receiving transducer signals for a subject and training a model for characteristics of a subject or subject group. The model is used in generating sleep data according to real-time correspondence and values of transducer signals including subject rib displacement, subject abdomen displacement, subject torso movement, and subject orientation. Combinations of the transducer inputs are used
(Continued)

to determine features from which outputs such as an AHI score are determined. A feature matrix is normalized based on dynamically-generated positional epochs bordered by subject movements to new positions and used to provide a normalization matrix.

20 Claims, 11 Drawing Sheets

(58) Field of Classification Search
USPC .......................................................... 600/534
See application file for complete search history.

(56) References Cited

U.S. PATENT DOCUMENTS

| | | | |
|---|---|---|---|
| 2014/0228657 A1 | 8/2014 | Palley et al. |
| 2014/0276175 A1 | 9/2014 | Banet et al. |
| 2014/0358014 A1 | 12/2014 | Heneghan et al. |
| 2015/0216424 A1 | 8/2015 | McMahon et al. |

FOREIGN PATENT DOCUMENTS

| | | |
|---|---|---|
| GB | 2520169 A | 5/2015 |
| WO | 2015/002940 A2 | 1/2015 |

OTHER PUBLICATIONS

Frank H. Wilhelm et al.; "Continuous Electronic Data Capture of Physiology, Behavior and Experience in Real Life: Towards Ecological Momentary Assessment of Emotion"; Interacting with Computers; Mar. 1, 2006; pp. 170-186; vol. 18, No. 2.

A. Roebuck et al.; "A Review of Signals Used in Sleep Analysis"; Physiological Measurement; Dec. 17, 2013; pp. R1-R57; vol. 35, No. 1.

Richard Hummel et al.; "Estimation of Sleep Status in Sleep Apnea Patients Using a Novel Head Actigraphy Technique"; 37th Annual International Conference of the IEEE Engineering in Medicine and Biology Society; Aug. 25, 2015; pp. 5416-5419.

Atena Roshan Fekr et al.; "Respiration Disorders Classification With Informative Features for m-Health Applications"; IEEE Journal of Biomedical and Health Informatics; May 1, 2016; pp. 733-747; vol. 20, No. 3.

Zachary T. Beattie et al.; "Classification of Lying Position Using Load Cells Under the Bed"; 33rd Annual International Conference of the IEEE Engineering in Medicine and Biology Society; Aug. 30-Sep. 3, 2011 pp. 474-477; Boston, MA, USA.

APPARATUS AND METHOD FOR DETECTION OF DYSFUNCTIONAL BREATHING

The invention relates to monitoring of respiratory effort, to detect breathing events or patterns indicative of dysfunctional breathing for example apnoea events during sleep or Cheyne-Stokes respiration. The invention relates primarily but not exclusively to monitoring of respiratory effort while the patient is relatively still such as while asleep or confined to bed or a chair for a prolonged period.

PRIOR ART DISCUSSION

US20140358014 (Heneghan et al.) describes a sleep monitoring system with sensors such as ECG and inductance plethysmography sensors, and a processor which extracts features which are then fed to a classifier in order to indicate the sleep stage of the patient.

US2011124979 (Heneghan et al.) describes the use of a Holter monitor and a pulse oximeter.

CN101569526 describes a sleep monitoring system which uses an inductive sensor for sensing respiratory breathing movement, an accelerometer for sensing physical movement of a patient and an ECG for heart activity using.

GB2396012 describes a respiration monitoring system using ultrasound transducers which are placed on the chest and abdomen to detect diaphragm movement.

GB2520169 describes a sleep monitoring system for detecting movement of a patient while sleeping, the sensors are embedded in the mattress.

US2015216424 describes detection of sleep, motion and breathing of a sleeping patient using radiofrequency transmitters.

U.S. Pat. No. 6,935,335 describes treating obstructive sleep apnoea by terminating an obstructive sleep apnoea event before the cessation of breathing occurs. The system comprises one or more microphones capable of detecting breathing sounds within an airway of a person.

The invention is directed towards providing more effective detection of breathing events or patterns indicative of dysfunctions in breathing for example apnoea events during sleep or Cheyne-Stokes respiration

SUMMARY OF THE INVENTION

A breathing monitoring method is performed by a monitoring system comprising a digital processor linked with transducers mounted on one or more substrates of a sensor device and adhered to a patient torso. The transducers may include transducers for sensing:
subject rib displacement,
subject abdomen displacement, in which the rib and abdomen transducers are located on a common substrate adhered to the subject's skin, and
subject movement causing subject body position change.
The method may include one or more of the following steps performed by the processor:
in a training phase, receiving signals from said transducers for one or more human subjects, and training a classification model for characteristics of a subject or subject group,
wherein for said training, the processor extracts features from the transducer signals, and performs comparisons with reference diagnostics data to provide the classification model, and wherein the reference diagnostics data includes one or any combination of apnoeic event timestamp, apnoeic event type, AHI score, patient position, activity level, sleep stage, wake and sleep time, desaturation events, breathing stoppage events, non-apnoeic breathing disorder events, EEG activity, heart rate, and/or cardiac events, and
in a use phase, the processor generating breathing event data according to values and real-time correspondence of said transducer signals, in which the subject movement signals are used to perform validation and cleaning of the rib and abdomen displacement transducer signals, and in which the processor performs positional normalisation to correct for subject movement to different positions.

Preferably, the subject movement signals are representative of movement in each of a plurality of dimensions, such as movement in all three dimensions X, Y, and Z.

Preferably, the subject movement transducers include an accelerometer, and this may be co-located with the rib and abdomen transducers.

The processor may also receive signals representative of subject blood oxygen level, and the processor is configured to use the blood oxygen level data to determine oxygen desaturation events.

Preferably, the processor automatically determines, from the subject movement transducer signals, if the subject has turned so that either the rib or abdomen displacement transducers have reduced function according to the subject movement signal. The processor may automatically identify sleep cycles per subject physical position.

Preferably, the processor automatically determines end of an apnoea event by detecting subject movement at the same time as rib displacement.

The processor may compute sporadic movement characteristics from the transducer signals.

Preferably, the processor computes from the transducer signals characteristics for correlation and covariance between displacement and movement signals, and performs secondary measurements of movements to provide breathing features to be extracted and compared.

Preferably, the processor computes from the transducer signals characteristics for detection of signal attenuation due to positioning of the sensor device.

Preferably, the processor is configured to:
generate subject rib and abdomen displacement features according to time-based windows, determine subject position after movement and use said positions as start and end events for positional epochs, and
normalise the displacement features of windows within said positional epochs.

Preferably, the processor is configured to perform said step of determining subject position data as derived data based on a plurality of transducer signals, and the derived data may be root mean square RMS data.

Preferably, the processor is configured to develop a normalisation matrix based on said positional epochs, and to apply said normalisation matrix to a time window-based feature matrix in order to normalise and correct the feature matrix for changes in position and the resulting changes in rib and abdomen displacement transducer function.

Preferably, the transducer signals are provided at a frequency in the range of 2 Hz to 200 Hz.

Preferably, said time-based windows overlap.

Preferably, the processor:
records data from the transducer signals and performs segmentation into windows of fixed time length,
extracts at least one feature for each window, normalises said features based on subject position, in which a threshold is applied according to transducer and if signal strength is below the threshold a normalisation factor of zero is applied and populates said feature matrix.

We also describe a breathing monitoring system comprising a digital processor linked with transducers mounted on one or more substrates of a sensor device configured to be adhered to a patient torso, said transducers including transducers for sensing:

subject rib displacement,
subject abdomen displacement, in which the rib and abdomen transducers are located on a common substrate adhered to the subject's skin, and
subject movement causing subject body position change;
wherein the digital processor is configured to perform steps of:
  in a training phase, receiving signals from said transducers for one or more human subjects, and training a classification model for characteristics of a subject or subject group,
  wherein for said training, the processor extracts features from the signals, and performs comparisons with reference diagnostics data to provide the classification model, and wherein the reference diagnostics data includes one or any combination of apnoeic event timestamp, apnoeic event type, AHI score, patient position, activity level, sleep stage, wake and sleep time, desaturation events, breathing stoppage events, non-apnoeic breathing disorder events, EEG activity, heart rate, and/or cardiac events, and
  in a use phase, generating breathing event data according to values and real-time correspondence of said transducer signals, in which the subject movement signals are used to perform validation and cleaning of the rib and abdomen displacement transducer signals, and in which the processor performs positional normalisation to correct for subject movement to different positions.

The system also includes in various examples components and functions as set out above and in the claims.

The invention also provides a non-transitory computer readable medium comprising software code for performing the steps of a method of any example when executed by a digital processor.

Additional Statements

According to the invention, there is provided a sleep monitoring method performed by a digital processor, comprising steps of receiving transducer signals for a subject, training a model for characteristics of a subject or subject group, and generating sleep data according to real-time correspondence and values of said signals.

In one embodiment, the transducer signals include:
subject rib displacement,
subject abdomen displacement
subject movement, and
subject orientation.

In one embodiment, the subject movement signals are representative of torso movement. Preferably, the subject movement signals are representative of movement in each of a plurality of dimensions, preferably all three dimensions X, Y, and Z. In one embodiment, the subject movement signals are received from an accelerometer. In one embodiment, the accelerometer is co-located with the rib and abdomen transducers.

In one embodiment, the rib and abdomen transducers are located on a common substrate adhered to the subject's skin.

In one embodiment, the processor also receives signals representative of subject blood oxygen level.

In one embodiment, the subject movement signals are used to perform validation and cleaning of the rib and abdomen transducer signals. In one embodiment, for training, the processor extracts features from the signals, and performs comparisons with reference diagnostics data to provide a classification model.

In one embodiment, the reference data includes one or any combination of apnoeic event timestamp, apnoeic event type, AHI score, patient position, activity level, sleep stage, wake and sleep time, desaturation events, breathing stoppage events, non-apnoeic breathing disorder events, EEG activity, heart rate, and/or cardiac events.

In one embodiment, the processor automatically determines if the subject has turned so that either the rib or abdomen transducers are not functioning according to the subject movement signal.

In one embodiment, the processor automatically identifies sleep cycles per subject physical position.

In one embodiment, the processor automatically determines end of an apnoea event by detecting subject movement at the same time as rib displacement.

In one embodiment, the processor computes one or more of the following characteristics from the transducer signals:
  positional normalisation, which allows correction for the positioning and relative signals of the device at different positions, and/or
  detection of sporadic movement, and/or
  correlation and covariance between piezo and accelerometer, which allows for secondary measurements of movements and breathing features to be extracted and compared, and/or
  detection of signal attenuation due to positioning of device.

In another aspect, the invention provides a sleep monitoring apparatus comprising a digital processor and a plurality of transducers, wherein the processor is configured to perform a sleep monitoring method comprising steps of receiving transducer signals for a subject, training a model for characteristics of a subject or subject group, and generating sleep data according to real-time correspondence and values of said signals.

In one embodiment, the transducers are arranged to detect subject rib displacement, subject abdomen displacement, subject movement, and subject orientation. In one embodiment, a transducer is configured to provide the subject movement signals representative of torso movement, preferably representative of movement in each of a plurality of dimensions, preferably all three dimensions X, Y, and Z. In one embodiment, said transducer is an accelerometer. In one embodiment, a transducer is a blood oxygen level sensor.

In one embodiment, the processor is configured to use subject movement signal to perform validation and cleaning of the rib and abdomen transducer signals. In one embodiment, the processor is configured to, for training, extract features from the signals and perform comparisons with reference diagnostics data to provide a classification model.

In one embodiment, the reference data includes one or any combination of apnoeic event timestamp, apnoeic event type, AHI score, patient position, activity level, sleep stage, wake and sleep time, desaturation events, breathing stoppage events, non-apnoeic breathing disorder events, EEG activity, heart rate, and/or cardiac events.

In one embodiment, the processor is configured to automatically determine if the subject has turned so that either the rib or abdomen transducers are not functioning according to the subject movement signal, and to automatically identify sleep cycles per subject physical position.

In one embodiment, the processor is configured to automatically determine end of an apnoea event by detecting subject movement at the same time as rib displacement.

In one embodiment, the processor is configured to compute one or more of the following characteristics from the transducer signals:
- positional normalisation, which allows correction for the positioning and relative signals of the device at different positions, and/or
- detection of sporadic movement, and/or
- correlation and covariance between piezo and accelerometer, which allows for secondary measurements of movements and breathing features to be extracted and compared, and/or
- detection of signal attenuation due to positioning of device.

DETAILED DESCRIPTION OF THE INVENTION

The invention will be more clearly understood from the following description of some embodiments thereof, given by way of example only with reference to the accompanying drawings in which.

Figure 11:
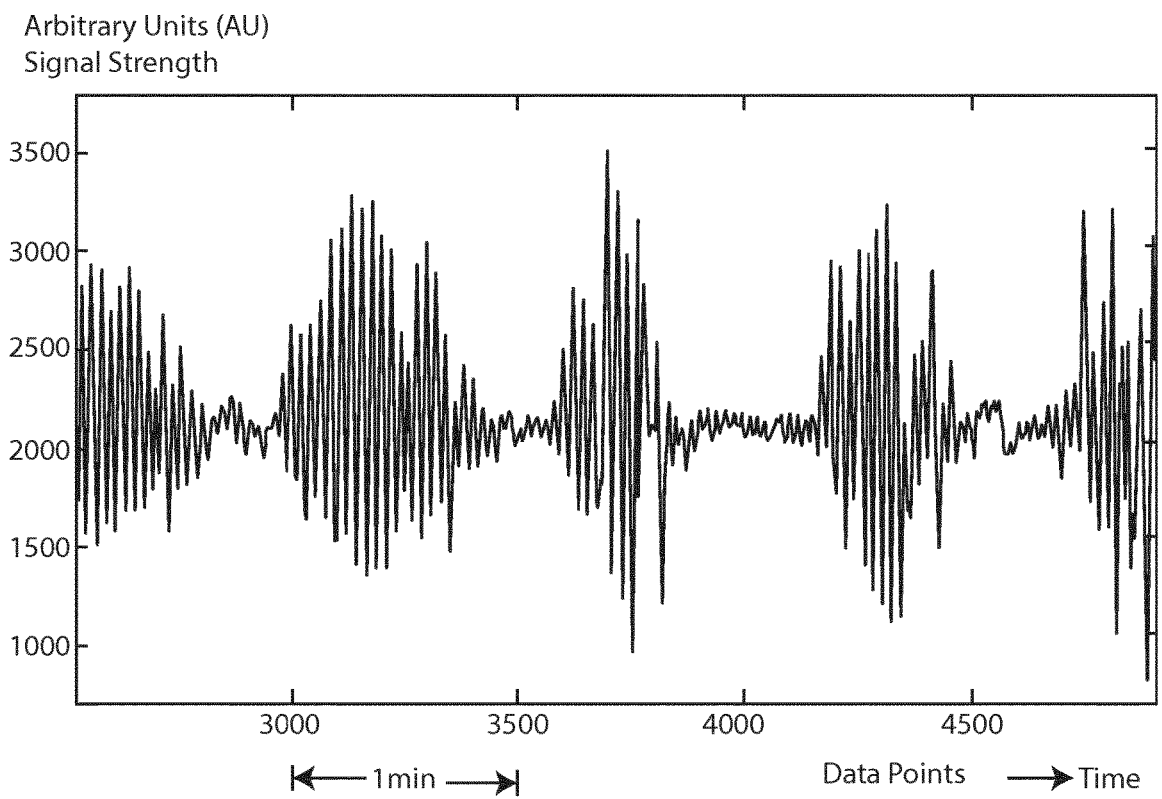
Figure 12:
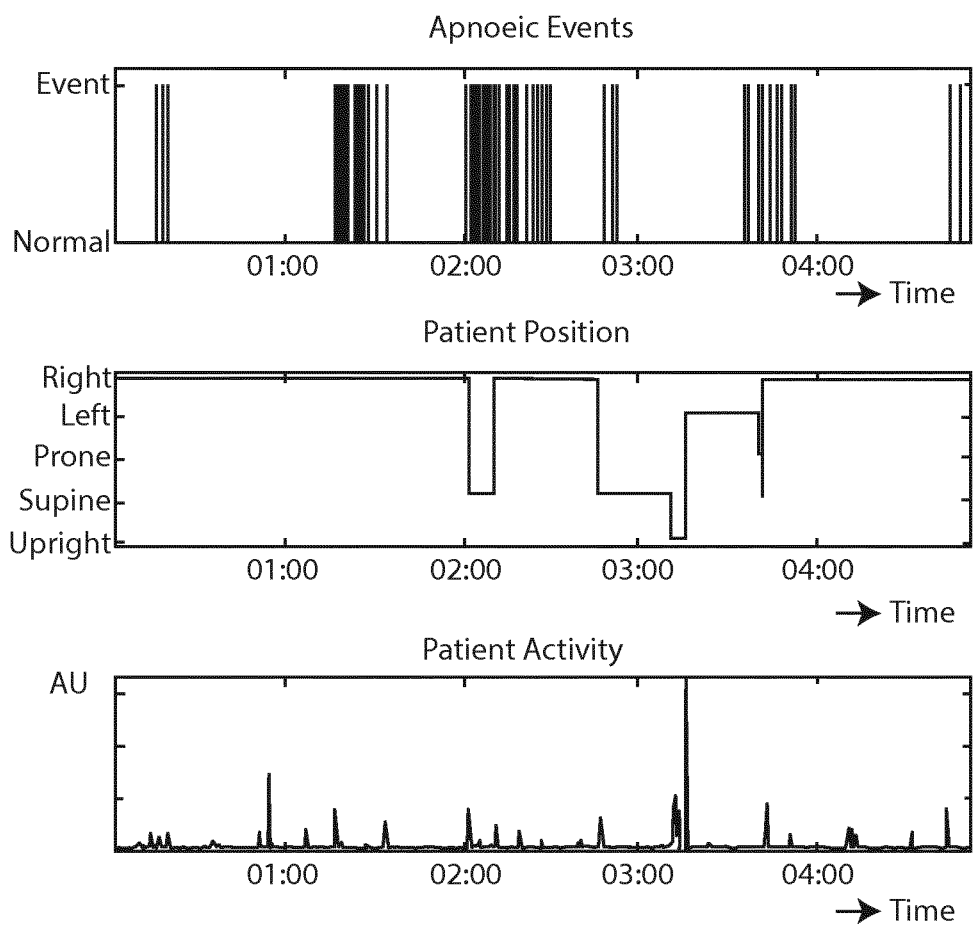

FIG. 11 is a plot showing a respiratory effort signal in which the respiratory effort increases from near zero to a maximum, then decreases again to almost zero over time periods of about 1 minute, a pattern which may be indicative of Cheyne-Stokes respiration; and FIG. 12 is a sample sleep report indicating the time and number of detected apnoeic events, the patient position, the patient activity level, study settings and patient details.

OVERVIEW

A respiratory effort monitoring method is performed by a digital processor, comprising steps of receiving transducer signals for a subject, training a model for characteristics of a subject or subject group, and generating dysfunctional breathing data according to real-time correspondence and values of said signals.

The reference data may include one or any combination of sporadic dysfunctional breathing event timestamps, normal breathing event timestamps, dysfunctional breathing event type, and/or positive diagnosis from medical professional.

The reference data may include one or any combination of epochs of respiratory effort data from a patient suffering a continuous dysfunctional breathing event, and positive diagnosis of dysfunction from a medical professional.

In one example, an algorithm executed by a digital processor to take results from multiple transducer arrays to detect differences in breathing patterns between different parts of a patient's body for example between the left and right sides of the patient's ribcage.

Figure 1:
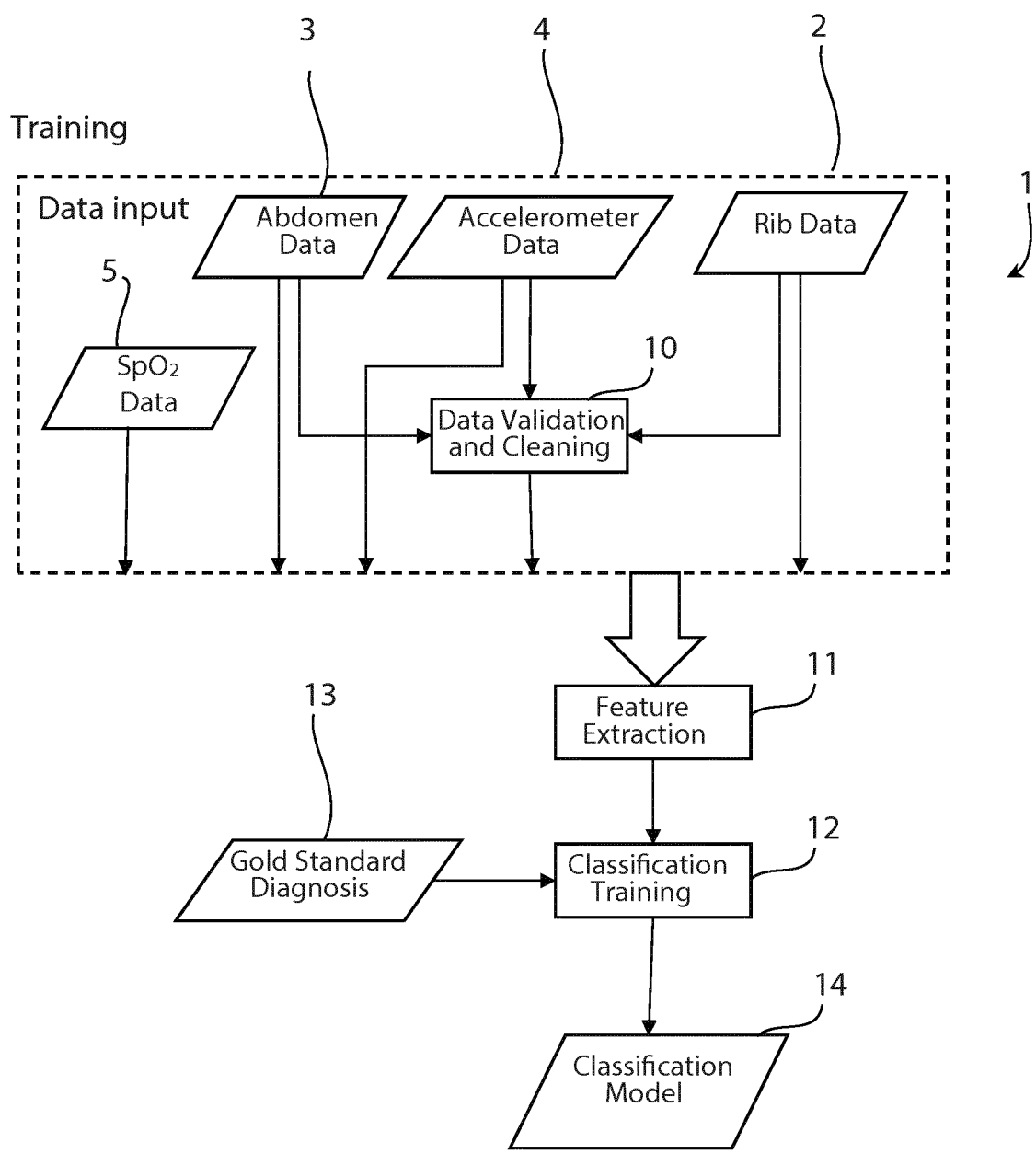
FIGS. 1 and 2 are flow diagrams showing the major sensor inputs and processing steps in a method for training a processor of a monitoring apparatus of the invention.
Figure 2:
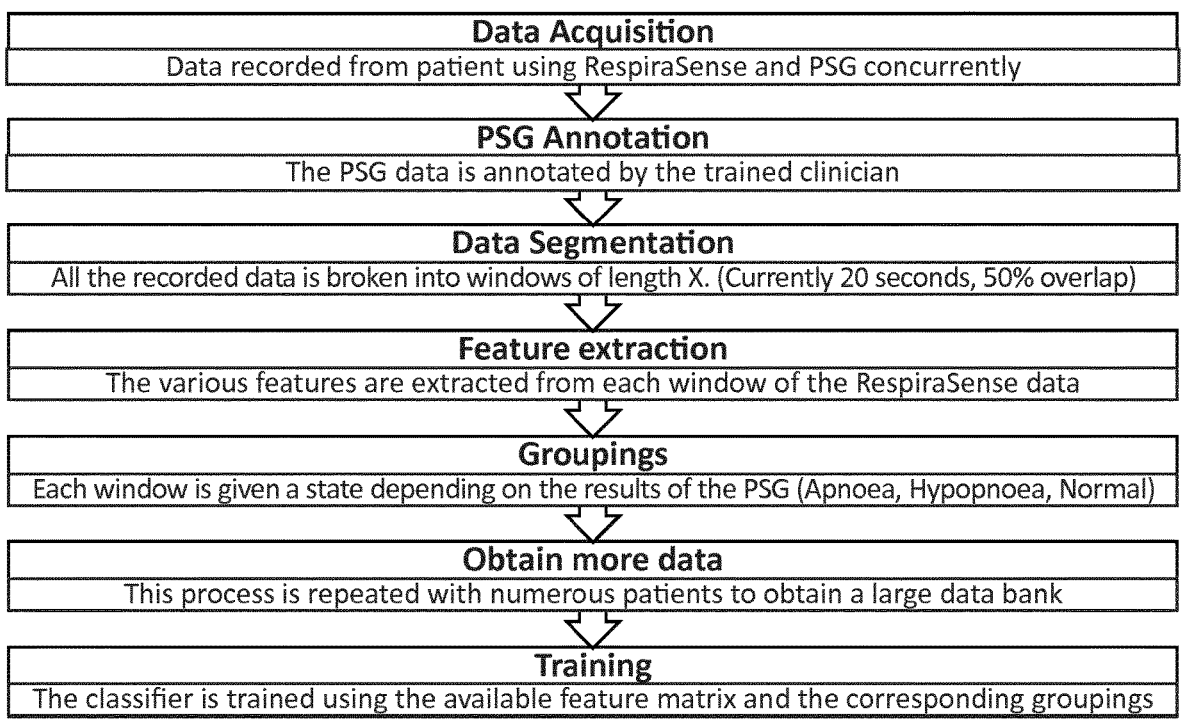

Referring initially to FIGS. 1 and 2 an apparatus of the invention comprises a processor hosted on a cloud-based PC or server, arranged to receive via wireless protocol or physical data transfer, signals from the following:

A strain gauge 2 placed by adhesion on the patient's rib cage. This comprises a capacitive transducer which a piezoelectric element at its core, in which a change in capacitance indicates displacement.

A strain gauge 3 of this type placed by adhesion on the patient's abdomen.

An accelerometer 4.

An $SpO_2$ monitor 5.

Time-stamps associated with each individual data point are collected from the four sensors 2 to 5 at a rate of 10 Hz, and more generally is preferably in the range of 2 Hz to 200 Hz In one embodiment, the data is first streamed to a tablet PC, then transferred via 3G to an Xampp protocol server hosted on a MacBook Pro PC™.

The initial data processing, for training of the device, includes feature extraction 11, classification training 12 using gold standard diagnosis data 13, and generation of a classification model in step 14. The feature extraction and classification steps 11 and 12 are shown in more detail in FIG. 2. Annotated gold standard data is received by the processor, including dysfunction event timestamps and dysfunction event type. Segmentation into windows of fixed time lengths is performed on transducer, accelerometer, $SpO_2$ and annotated data. These time segments may overlap. Each window (or "segment") is given a state based on the gold standard data. This is repeated for many patients to provide a large matrix of features with corresponding states. The random forest classifier is then trained using the available feature matrix and corresponding groupings.

Before describing the training and operation of the device in more detail, the following describes in more detail the physical sensor device components.

Sensor Devices

The sensor may have a disposable substrate for adhering to a patient torso and a re-usable electronics controller adhered to the substrate. The substrate may comprise a body within which are embedded elongate transducers for measuring deformation (or "displacement"). These are linked by conductors to the controller. The controller preferably comprises a plastics housing containing a circuit board and a rechargeable battery, and an alarm sounder. There may be a connector for wired connection to an external device or host system and/or a wireless interface such as a Bluetooth interface for wireless communication.

The controller may be mechanically joined to the substrate for removal and re-use, which is useful in a medical application where consumable body contact sensors are desired to be for single patient single use.

The transducers may comprise a piezoelectric film sandwiched between:
a coating ink pattern, and a positive ink pattern on top; and
a negative ink pattern and a Mylar layer underneath.

The composition of the transducer is therefore a multi-layer piezo stack separated by a metal foil. In this embodiment the piezo stack is a multi-purpose, piezoelectric transducer for detecting physical phenomena such as vibration or impact or general deformation. The piezo film element is laminated to the sheet of polyester (Mylar), and produces a usable electrical signal output when forces are applied to the sensing area. This compositional stack is heat-laminated using a translucent polymer. Each piezo film layer is partially extended to form a terminal by which a clamp is fixed to. This provides a secure electrical contact for the instrumentation amplifier circuitry.

The substrate body comprises polypropylene clear release film, 3M™ medical grade silicone adhesive, and a polyester layer. The transducers are located between the adhesive and the polyester layers.

The transducers may be of equal length, width, thickness, and composition, positioned 30° apart from one another about a single point of common placement which ensures a preferred form factor. The angle between each transducer can be different and indeed they may be parallel. However the preferred range is 25° to 55°, and the most preferred is in the region of 27° to 33°. The preferred length and width of each transducer is in the range of 30 mm to 50 mm and 50-400 µm thick.

The transducers provide deformation information to allow the processor to automatically generate an output indicating patient respiration. However, the accelerometer allows improved effectiveness in analysing signals arising from wearer's activity and posture. Such variables of posture and activity have direct influence upon the effectiveness of the system. Data from the transducers may be used to identify how quickly the human subject is moving, and the subject's posture and when movement-based artefacts have been induced in the strain transducer signal. This further enables the human subject to live a normal functional life while the device comprehensively measures the respiratory performance without imposing limitations.

The displacement transducers are particularly responsive to a distending movement of the rib cage, forwardly and laterally. This is almost entirely due to respiration. There may also be pivoting due to motion artefacts such a walking. One transducer is approximately equally responsive to rib distending and motion artefacts, whereas the other transducer is less responsive to rib distending and equally responsive to the motion artefacts. When the subject changes their posture, and/or begins breathing under a different regime (normally chest breathing or diaphragm breathing) the signal expressed on the transducers can change greatly. Typically the transducer which is resting on the rib responds with greater magnitude when the subject is upright and/or breathing mostly using chest movements. When the subject is lying and/or diaphragm breathing the transducer, resting on the abdomen, typically responds more strongly. In atypical cases, for instance when the subject is breathing heavily using the ribs, the respiratory response from a transducer can be of such small magnitude as to be indistinguishable from background noise. In this event, the data from this transducer or 6 is discarded, and the other transducer is used solely to derive the respiratory rate.

It is preferred that the displacement gauges 2 and 3 and the position-sensing accelerometer 4 are mounted physically on the same substrate. A suitable way to achieve this is to use a sensor as described in our prior PCT patent specification number WO2014/128090, the contents of which are incorporated herein by reference. This sensor adheres as an integral substrate onto the patient's torso, with a top sensor part over a lower rib, a bottom sensor part over the adjacent part of the abdomen, and the accelerometer being supported on the main body of the substrate.

Figure 3:
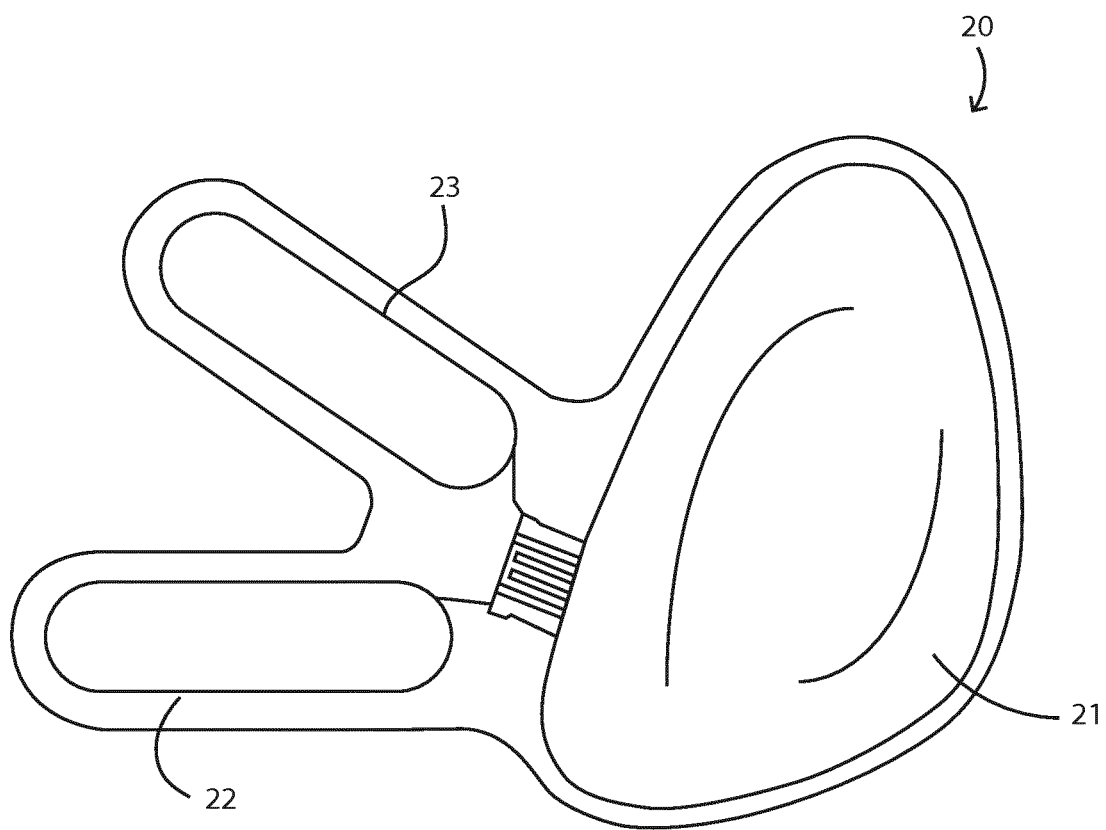
FIG. 3 is a front view of a sensor device and a reusable electronics housing which may be applied to a patient to monitor patient breathing.

FIG. 3 shows a sensor device 20, having two arms 22 and 23 for attachment to a patient at the region of the boundary between the ribs and the abdomen, and incorporating the sensors 2 and 3. The device 20 includes an electronics unit 21 incorporating the circuit 10 and the accelerometer 4, and the $SpO_2$ sensor 5. The unit 21 communicates wirelessly with a host, in one example via Bluetooth to a Tablet PC.

Figure 4:
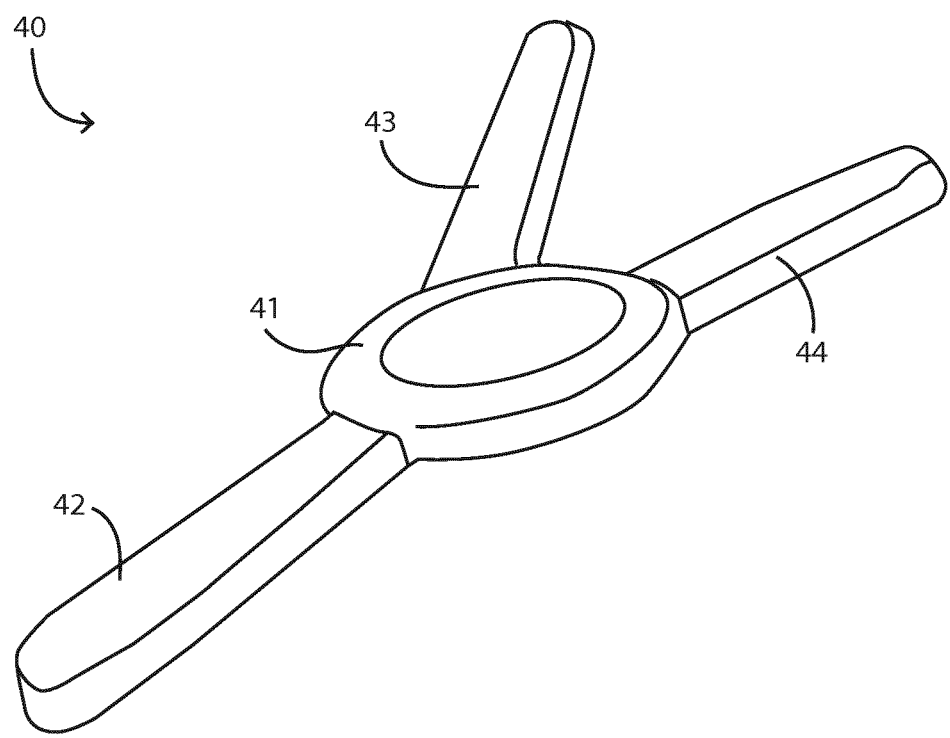
FIG. 4 is an isometric view of variation of an alternative device, in which a third arm holds an $SpO_2$ monitor and/or any other sensor such as an ECG electrode.

FIG. 4 shows an alternative sensor device, 40, which is a variation on the sensor device shown in FIG. 3. This comprises a central hub 41 for electronics, and three radially-extending arms 42, 43, and 44. The arms 43 and 44 have strain gauges for displacement detection as described above, and the arm 42 houses an auxiliary sensor such as an $SpO_2$ monitor or part of an ECG.

It has been found that with the rib and abdomen displacements being monitored using devices as described above accurate data is received in real time. This is primarily because the immediate proximity of the sensors allows for correlation to be performed between the sensors. Hence, differences and similarities between breathing signals at each location can be easily compared. Secondly, the position and orientation of the sensors allows either sensor to continue to record data when the other is compromised by patient interference.

Moreover with accelerometer data for three axes coming from the same location, the rib and abdomen data can be very effectively weighted to compensate for overall patient movement. The immediate proximity of the sensors and accelerometer allow for correction and correlation to be performed on all sensor and accelerometer signals at once. Hence, movement artefacts may be easily separated from breathing signals, and breathing signals can be easily correlated across the different piezo signals. In general, the accelerometer provides overall patient movement or "position" data.

There is therefore a total of six signals received in real time: $SpO_2$, abdomen displacement, rib displacement, and patient torso overall X, Y, and Z position.

Training

Prior to use, the system must first be trained, and this may be done using data from a gold standard for AHI calculation, and/or from polysomnography (PSG) data.

A PSG will typically record a minimum of 12 channels requiring a minimum of 22 wire attachments to the patient and is performed within a sleep laboratory. The data obtained from the PSG is analysed post-recording by a trained sleep clinician and all epochs of data where an apnoea/hypopnoea event are detected are annotated.

In order to train the system 1, the sensor is also attached to the patient during the PSG. Therefore, the two recordings are collected concurrently. The annotated PSG data is then used to specify where, in the system 1 data, apnoea or hypopnoea events were said to have occurred. Once these epochs are known, and multiple patients have been analysed, the system 1 can be trained using comprehensive machine learning techniques described below to provide a classifier for on-going use of the system.

The choice of features to extract has a large impact on the accuracy of the final classifier. No matter how good the classifier, if there is not enough information in the extracted features to separate the different events required then the classifier will be unable to do so. Therefore, the choice of features is very seldom ever completed. There are always better features to choose.

These features are extracted from each window (bin) of data separately (for example, 20 seconds of data). Further, most of these features are also extracted from each data stream which is available, i.e. the three accelerometer (providing position data arising from subject movement) signals, the two piezo (deformation transducers providing rib and abdomen displacement data) signals and possibly the $SpO_2$ signal. Table 1 below lists features used in one embodiment. In the Transducer column Pr and Pa refer to the rib and abdomen piezo signals, S refers to $SpO_2$, and X, Y, and Z refer to the three orthogonal accelerometer signals. Features are studied using differing techniques to ensure best representation of that feature in training data.

TABLE 1

Feature List

| Feature Name/Description | Transducers used |
| --- | --- |
| Energy and amplitude of transducer signals | |
| Breathing amplitude (Root Mean Square (RMS), standard deviation) | Pr, Pa, X, Y, Z |
| Movement amplitude (Root Mean Square (RMS), standard deviation) | X, Y, Z |
| Signal Energy | Pr, Pa, X, Y, Z |
| Signal Energy compared to surrounding bins | Pr, Pa, X, Y, Z |
| Signal Energy compared between signals | Pr, Pa, X, Y, Z |
| Statistical Measurements of transducer signals | |
| Low order statistical variation (Minimum, median, maximum, quartiles, mean, trimmed mean) | Pr, Pa, X, Y, Z, S |
| High order statistical variation and distribution shape (standard deviation, kurtosis, skewness) | Pr, Pa, X, Y, Z, S |
| Correlation coefficients (normal and absolute, all combinations) | Pr, Pa, X, Y, Z, S |
| Patient Position | |
| Patient Position | X, Y, Z |
| Change to body position in current bin | X, Y, Z |
| Change to body position from previous bin | X, Y, Z |
| Change to body position from next bin | X, Y, Z |
| Positional Normalisation (Normalisation of features based on position of patient) | |
| Blood Oxygenation Measurements | |
| $SpO_2$ Desaturation event | S |
| $SpO_2$ Compared to previous bin | S |
| $SpO_2$ Compared to next bin | S |
| $SpO_2$ Normalisation event | S |
| Breathing Features | |
| Mean Respiratory Rate | Pr, Pa, X, Y, Z |
| Respiratory rate changes in bin | Pr, Pa, X, Y, Z |
| Respiratory rate changes between bins | Pr, Pa, X, Y, Z |
| Sporadic Respiratory Events | Pr, Pa, X, Y, Z |
| Respiratory pattern changes in bin | Pr, Pa, X, Y, Z |
| Respiratory pattern changes between bins | Pr, Pa, X, Y, Z |
| Frequency and Spectrum Analysis | |
| Wavelet decomposition to level 6 | Pr, Pa, X, Y, Z |
| Fourier Analysis | Pr, Pa, X, Y, Z |
| Other Features | |
| Detection of sporadic movement | X, Y, Z |
| Accelerometer - Piezo Correlation | Pr, Pa, X, Y, Z |
| Movement - Breathing correlation | Pr, Pa, X, Y, Z |
| Detection of signal attenuation | Pr, Pa, X, Y, Z |
| Sleep/Wake detection in bin | Pr, Pa, X, Y, Z |
| Sleep/Wake change between bin | Pr, Pa, X, Y, Z |

Therefore, as can be seen from the table, each window of data currently has over 120 features describing the data within that window.

Referring again to FIGS. 1 and 2 there is feature extraction in step 11, classification training in step 12, and gold standard diagnostics inputs received in step 13. These provide a trained classification model in step 14. The gold standard data includes timestamps of apnoeic events detected using current gold standard or medically accepted techniques. The data may also include data from multiple sensors such as:

Respiratory inductance plethysmography (movements of respiration)
Nasal airflow/pressure
Electroencephalogram (EEG)
Electrocardiography (ECG)
Accelerometer measurements
Blood Oxygenation level ($SpO_2$)

The respiratory data is first compared with the accelerometer data at the data validation and cleaning stage 10. Data from all of the modalities are then used to create features within the feature extraction stage 11. The resulting features are passed to a classification training stage 12, where the features are used to train a model to match the results outputted from the "gold standard diagnosis".

The classification model parameters are then available in step 14. These parameters, which are calculated during the training phase, are then used to determine the state of any new data provided. The "gold standard diagnosis" is a hospital or home-based sleep test, scored by a trained medical sleep technician. In general, the gold standard outputs include the following:

Apnoeic event timestamp
Apnoeic event type
AHI (Apnoea-Hypopnoea Index) Score
Patient Position
Activity level
Sleep stage
Wake/Sleep time
Desaturation events
Breathing stoppage events
Non Apnoeic breathing disorder events
EEG activity
Heart rate
Cardiac events The feature extraction and classification training steps 11 and 12 involve recording the data from the sensors 2, 3, 4, and 5. PSG data from a patient is annotated by the clinician, and it is then segmented into windows of length X, say 20 seconds. There is in one embodiment an overlap in each window of, for example, 50%. The features are extracted for each window, and each window is given a state depending on the PSG results. Examples of states are "Apnoea", "Hypopnoea", and "Normal", though in some cases a further delineation of events may be made, for example "Central Apnoea" or "Obstructive Apnoea". This is repeated for in excess of 80 patients to build up a data bank which is saved to a database. A classifier, for example a random forest classifier, is then trained using the available data from this database.

The states associated with each window include one or any combination of:
- sporadic dysfunctional breathing event timestamps,
- normal breathing event timestamps,
- dysfunctional breathing event type, and/or positive diagnosis from a medical professional.
- epochs of respiratory effort data from a patient suffering a continuous dysfunctional breathing event,
- positive diagnosis of dysfunction from medical professional.

In one embodiment, the algorithm is configured to take results from multiple transducer arrays to detect differences in breathing pattern between different parts of a patient's body, for example between the left and right sides of the patient's ribcage.

Use of System, Real Time Data Analysis

Figure 5:
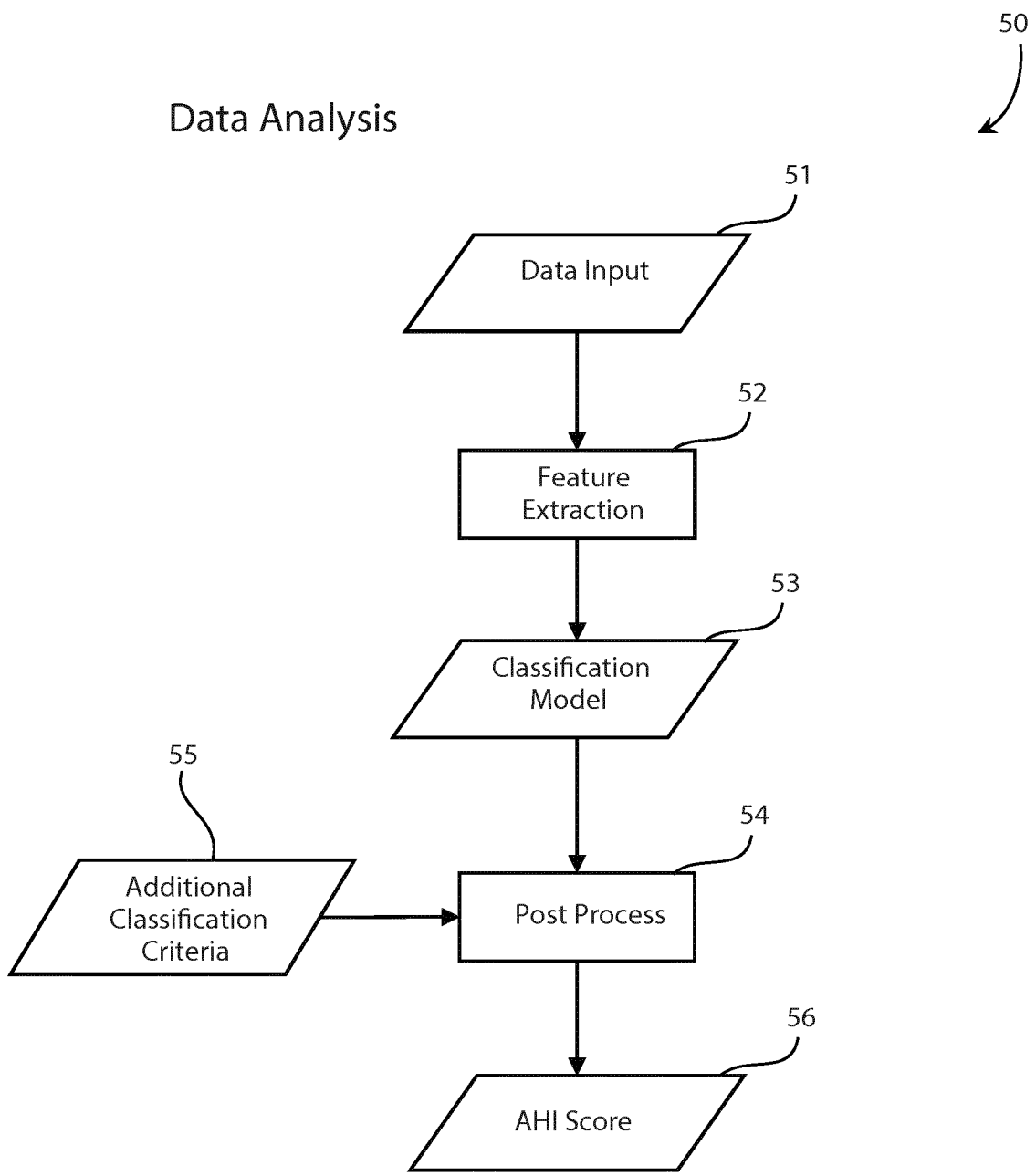
FIG. 5 is a flow diagram showing the major steps for operation of the processor.
Figure 6:
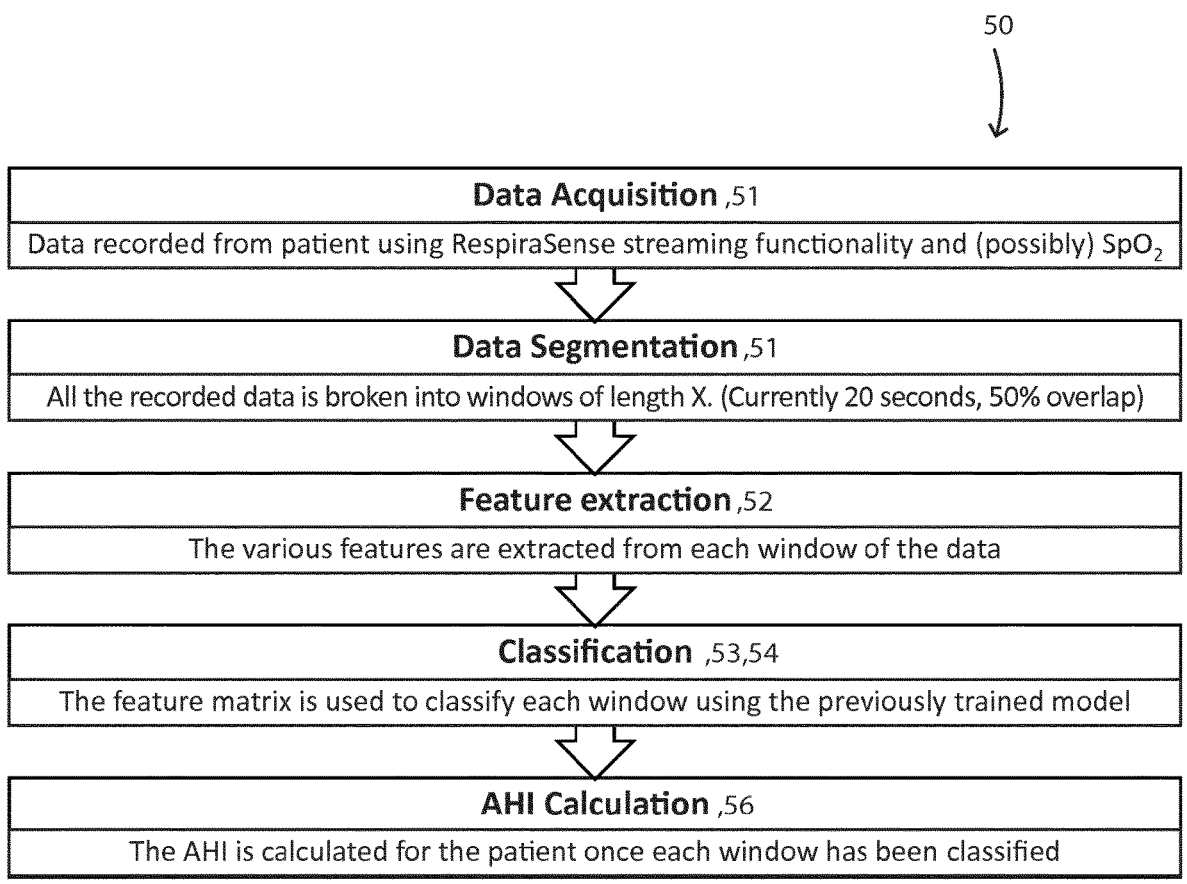
FIG. 6 is a more detailed flow diagram illustrating some of the steps.

The system is used most effectively when a patient is asleep or at rest in a bed or chair with little motion. Referring to FIGS. 5 and 6, in step 51 the data is collected, pre-processed and passed to feature extraction as in the training phase 1. Extracted features are processed by the trained classification model in step 53 and the windows (fixed time length) of data where apnoeic events may have occurred are determined. In step 54 detected events are compared with additional criteria (55) external to the machine learning process, and epochs are merged into events. An AHI value is calculated in step 56 and passed to a server for presentation.

The shape and location of the sensor device offers several avenues for advantageous algorithmic properties to be applied to the sensor data. Due to the positioning of the sensors respiratory data can be directly compared to:
 a. Improve the separation of respiratory signals from movement signals.
 b. Provide secondary information on breathing rate and features from the accelerometer.
 c. Ascertain when position of the patient has changed (subject movement).
 d. Ascertain when the patient is awake or asleep.

Due to the positioning of the sensor, at times either of the incoming displacement (deformation strain gauge transducer) signals can be attenuated by the patient lying on the device. This can be seen in FIG. 7, the data of which represents an abrupt change in position of a patient. The data was collected during a clinical investigation into the use of the device for detection of sleep apnoea. A change in position (subject movement) occurs at the halfway point in the data stream. Before the change, both rib and abdomen sensors (upper and lower legs) are picking up large amplitude respiratory signals. After the change, the upper (rib) leg is attenuated to nearly zero, while the lower (gut, abdomen) sensor continues to function. Due to this, the following algorithmic developments are preferably employed:
 a. Secondary indication of position changes from the strain gauge transducers.
 b. Separation of sleep cycle by position.
 c. Normalisation of signal features by position.
 d. Separation of dead signal from apnoeic signal.

Figure 7:
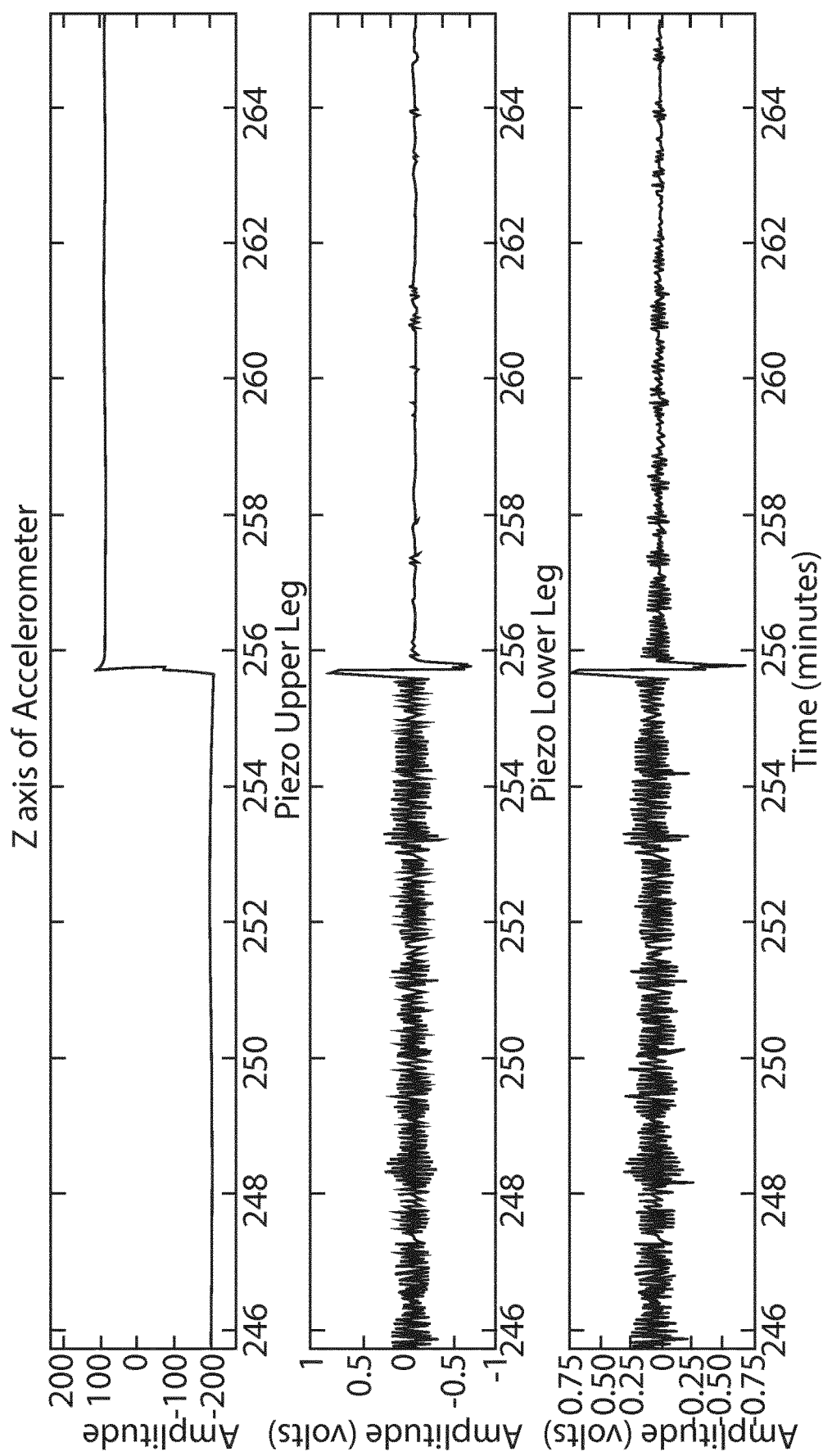
FIG. 7 is a set of plots showing corresponding variations with time of accelerometer Z-axis, and corresponding rib and abdomen displacement signals provided by piezoelectric capacitive transducers to the processor, to illustrate variable boundaries between positional epochs, triggered by positional changes of the patient.

These steps use a positional epoch, which is bordered at each end by a positional change, such as the positional change shown shortly before 256 minutes in FIG. 7. This positional change is used to normalise the features which have been extracted.

Figure 8:
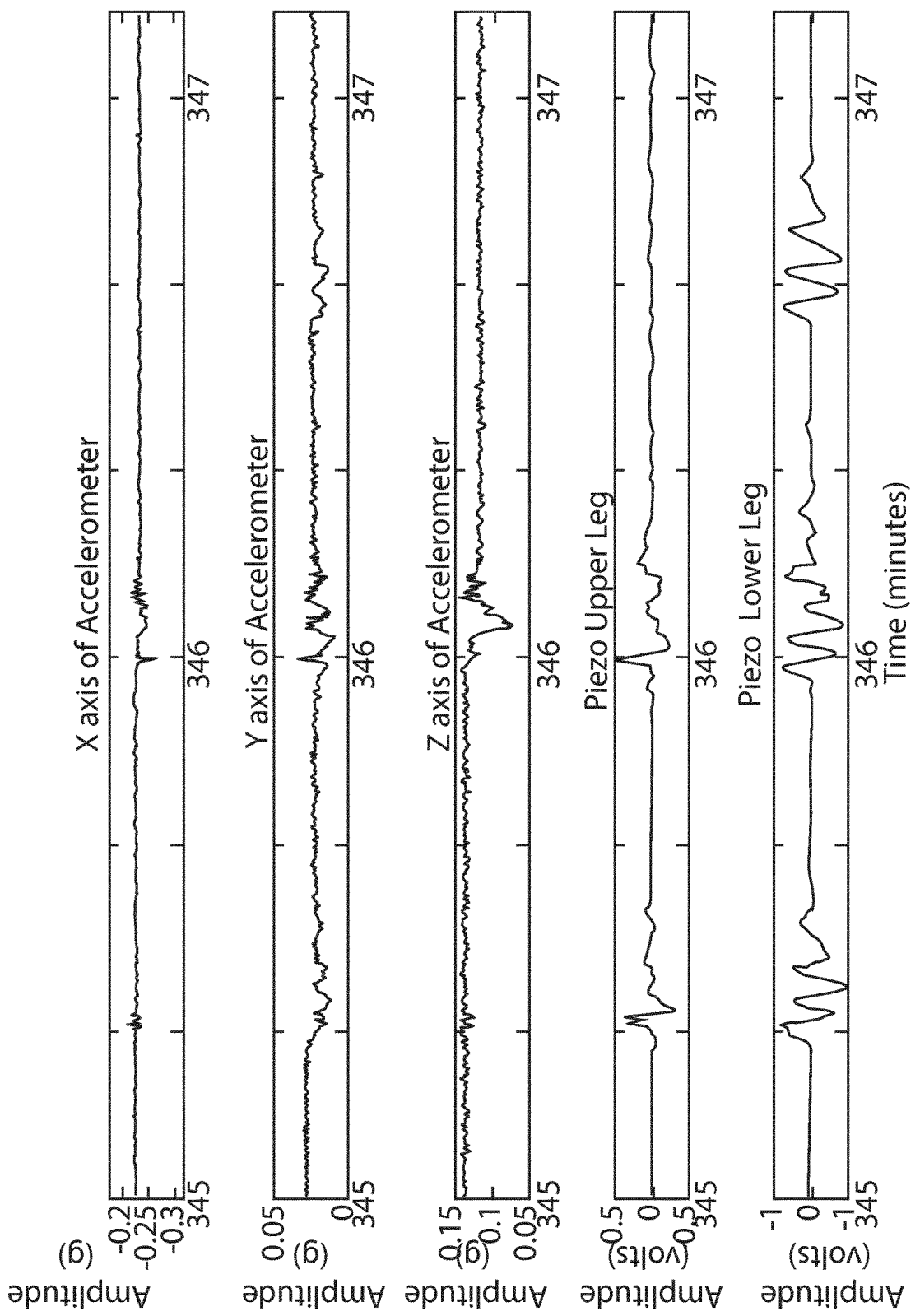
FIG. 8 is a set of plots showing corresponding variations with time of accelerometer X, Y, and Z axis position on a rib, and corresponding rib and abdomen displacement signals monitored by the processor, including signals indicative of potential apnoeic events.

The accelerometer also provides additional information regarding the cessation of apnoeic events such as those shown in FIG. 8, the data of which represents a period of time in which a patient repeatedly stops breathing while asleep. The data was collected during a clinical investigation into the use of the device for detection of sleep apnoea. It can be clearly observed that when the patient exits the event at time 346 minutes there is also a movement visible on the accelerometer axis. This is attributed to the initial restart of breathing and also could be due to the patient being slightly woken due to the apnoeic event. Again, this may trigger start of a positional epoch.

Figure 10:
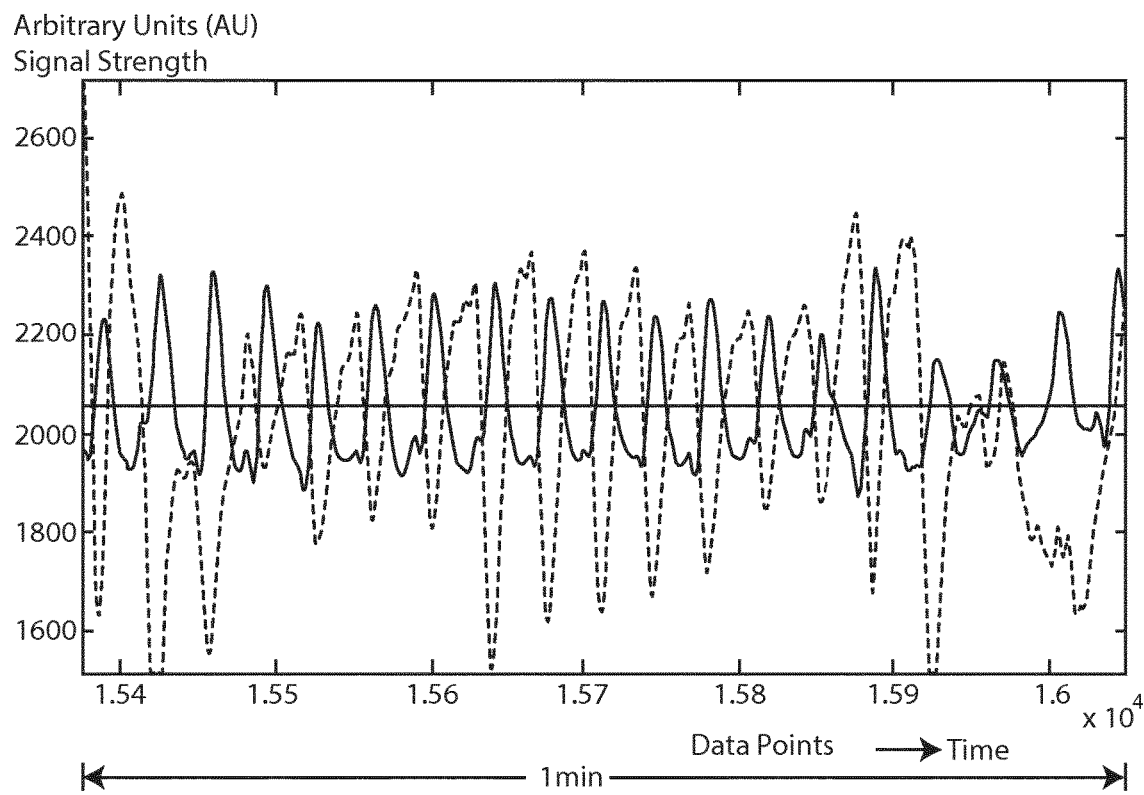
FIG. 10 is a plot showing rib and abdomen data where the rib (full line) and abdomen (dashed line) displacements are moving out of sync with one another, indicating a possible clinical adverse event.

Further dysfunctional breathing signals may be seen in the deformation transducer signals. Examples of this can be seen in FIGS. 10 and 11. FIG. 10 shows a period of "paradoxical breathing" where the ribs and abdomen move in opposite directions from one another. FIG. 11 shows signals indicative of Cheyne-Stokes Breathing, where the amplitude of the breathing effort trace slowly oscillates over time.

Important combinations of features are:
- Positional normalisation which allows correction for the unique positioning and relative signals of the device at different positions
- Detection of sporadic movement
- Correlation and covariance between deformation transducers (piezo) and accelerometer, which allows for secondary measurements of movements and breathing features to be extracted and compared
- Detection of signal attenuation due to positioning of device and subject movement such as turning so that he or she lies on the device and hence affecting the deformation signals.

The wavelet decomposition features include the final approximation coefficient at level 6 and all detail coefficients of each stage.

Figure 9:
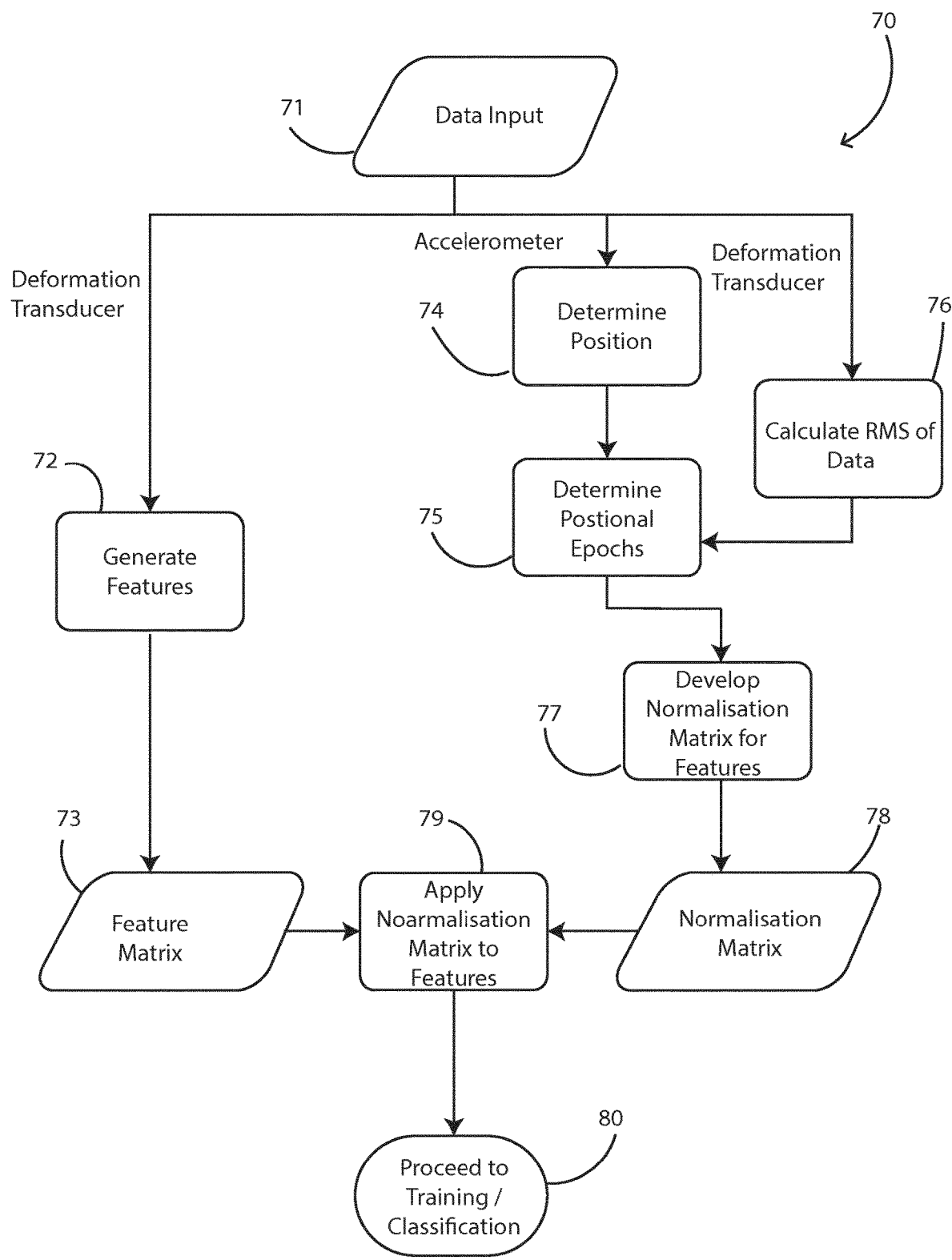
FIG. 9 is a flow diagram showing the major steps involved in generating features from the available data, determining positional epochs and normalising the features using positional information.

FIG. 9 is a flow diagram showing the major steps 70 involved in generating the features for inputted data, normalising by position and generating normalised features from that data. The data is then passed to the training/classification stage for classification based on a normalised matrix and feedback for training updating. There is data input in step 71, followed by a number of threads in parallel, as follows:
 (a) Use inputs from the deformation transducers (subject displacement) in step 72 to generate in step 73 a feature matrix.
 (b) Use accelerometer inputs in step 74 to determine position of the patient in each fixed-length time window (or "segment"), and from that determine positional epochs in step 75 when the patient's position is impacting on the generated displacement signals in a similar manner
 (c) Calculate in step 76 a root mean square ("RMS") of the deformation transducer signals, which provides the signal condition of the piezo data, and feed this data into the step 75 of determining positional epochs.
 (d) There is then a step 77 of developing a normalisation matrix for features, providing the signal condition of the piezo data, expressed as for example RMS, standard deviation or signal to noise ratio per positional epoch. The conditioning factors for each positional epoch are applied to each data segment for each extracted feature in 73 to create the normalisation matrix 78.

(e) The normalisation matrix is used together with the feature matrix in step 79 to provide in step 80 data features, normalised and corrected for the impact that patient position has on the piezo signals recorded by the device, and being available for training feedback also.

For the step 77 the processor develops a normalisation matrix for the features, in which for each feature in the feature matrix (73) an appropriate weighting based on the most appropriate of the signal condition measures generated in (b) is applied in step 79. For example, the signal amplitude feature may be normalised by the RMS of the appropriate time frame, while the contribution of frequency feature may be weighted to zero in cases where the signal to noise ratio is deemed too low to use that feature.

This normalisation matrix 78 is applied to the feature matrix, developed in step (c), in order to provide a feature matrix which accurately reflects signal parameters, with variations caused by patient position removed. This data can be then used for on-going data processing in use.

Referring to FIG. 7 for example and taking six 2-minute segments between minutes 250 and 262, it can be seen that a change in position happens at minute 256 (FIG. 9, 74). Taking the RMS of each 2-minute segment (here referred to as segments 1 to 6) (FIG. 9, 76):

|  | Segment: | | | | | |
| --- | --- | --- | --- | --- | --- | --- |
|  | 1 | 2 | 3 | 4 | 5 | 6 |
| Piezo 1 RMS | 380 | 410 | 410 | 5 | 3 | 7 |
| Piezo 2 RMS | 180 | 170 | 250 | 30 | 20 | 10 |

Separating the segments into two positional epochs (FIG. 9, 75), one before the position change and one after, we get the mean RMS of each positional epoch (FIG. 9, 77):

|  | Mean Before | Mean After |
| --- | --- | --- |
| Piezo 1 RMS | 400 | 5 |
| Piezo 2 RMS | 200 | 20 |

In this example, the positional epoch is determined solely by position, but in another embodiment, the positional epoch may be further delineated by other measures, such as detection of subtle changes in orientation of the patient.

A threshold is placed on the RMS of the signal strength, in this case, any normalisation factor less than 10 is set to zero to indicate that the data is too poor to use. This positional epoch data is then segmented into the same windows as used previously to segment data (FIG. 9, 78):

|  | Segment: | | | | | |
| --- | --- | --- | --- | --- | --- | --- |
|  | 1 | 2 | 3 | 4 | 5 | 6 |
| Piezo 1 Norm | 400 | 400 | 400 | 0* | 0* | 0* |
| Piezo 2 Norm | 200 | 200 | 200 | 20 | 20 | 20 |

*Note: 4-6 set to zero due to threshold

The feature matrix (FIG. 9, 73) is then modified (FIG. 9, 79) by dividing by the normalisation matrix (FIG. 9, 78) resulting in a modified feature matrix which is sent to training or classification (FIG. 9, 80). In this example, the feature matrix is represented simply by the piezo RMS values.

|  | Segment: | | | | | |
| --- | --- | --- | --- | --- | --- | --- |
|  | 1 | 2 | 3 | 4 | 5 | 6 |
| Piezo 1 RMS Feature Mod | 0.95 | 1.025 | 1.025 | 0* | 0* | 0* |
| Piezo 2 RMS Feature Mod | 0.9 | 0.85 | 1.25 | 1.5 | 1 | 0.5 |

*Note: 4-6 set to zero due to threshold

FIG. 10 is a plot showing rib and abdomen data where the rib and abdomen are moving out of synchronisation with one another. The X-axis represents a number of data points collected, while the Y-axis is measured in arbitrary units indicative of the breathing effort.

FIG. 11 is a plot showing a respiratory effort signal in which the respiratory effort increases from near zero to a maximum, then decreases again to almost zero over long time periods, a pattern which may be indicative of Cheyne-Stokes respiration. The X-axis represents a number of data points collected, while the Y-axis is measured in arbitrary units indicative of the breathing effort.

FIG. 12 is a sample sleep report indicating the time and number of apnoeic events detected, the patient position, the patient activity level, study settings and patient details. Advantageously, this provides patient position and other activity correlated to the events such as apnoeic events.

Advantages

The system accurately detects dysfunctional breathing irrespective of patient position, primarily due to positional epoch detection. The positional epochs are used to determine appropriate feature normalisation criteria to correct for changes in positions and resulting changes in piezo transducer function.

The system can be used to replace standard Home Sleep Test apnoea detection equipment, is less bulky, weighs less and is not prone to slippage like HST equipment.

Due to discrete nature of the device, the system is less likely to cause sleep disturbances than HST equipment.

The invention is not limited to the embodiments described but may be varied in construction and detail. For example, sensors other than piezoelectric transducers may be used to detect displacement, such as strain gauge. Also, the sensors may be mounted of physically separate substrates, although it is advantageous that they are on a common substrate.

The invention claimed is:

1. A breathing monitoring method performed by a monitoring system comprising a digital processor linked with transducers mounted on one or more substrates of a sensor device, said transducers including:

rib transducers for sensing rib displacement of a human subject, abdomen transducers for sensing abdomen displacement of the human subject, and movement transducers for sensing movement causing a body position change of the human subject, the rib and abdomen transducers being located on a substrate of the one or more substrates configured to adhere to skin of the human subject;

the method comprising steps of the processor:

in a training phase;
  receiving training signals from a first set of the transducers for one or more training human subjects, wherein the first set of the transducers mounted on the one or more substrates of the sensor device are configured to adhere to a torso of the one or more training human subjects, and;
  extracting features from the training signals;

performing comparisons with reference diagnostics data to provide a classification model, wherein the reference diagnostics data includes one or any combination of apnoeic event timestamp, apnoeic event type, AHI score, patient position, activity level, sleep stage, wake and sleep time, desaturation events, breathing stoppage events, non-apnoeic breathing disorder events, EEG activity, heart rate, and/or cardiac events; and training the classification model for characteristics of a user human subject; and in a use phase;

applying a second set of the transducers to the user human subject;

receiving use signals from the second set of the transducers, wherein the second set of the transducers mounted on the one or more substrates of the sensor device are configured to adhere to a torso of the user human subject;

generating breathing event data according to real-time receipt of the use signals from the second set of the transducers, the generating breathing event data including:

using movement signals from movement transducers of the second set of transducers to perform validation of rib displacement signals from rib displacement transducers of the second set of transducers and abdomen displacement signals from abdomen displacement transducers of the second set of transducers, respectively, wherein the using includes:

generating rib and abdomen displacement features of the user human subject according to time-based windows, determining data for positions of the user human subject after movement and using said positions as start and end events for positional epochs, wherein said data is derived based on the use signals from the second set of transducers, and performing positional normalisation to correct for movement causing a body position change of the user human subject, wherein the performing positional normalization includes:

normalizing the rib and abdomen displacement features of the time-based windows within said positional epochs, developing a normalisation matrix based on said positional epochs, and applying said normalisation matrix to a time window-based feature matrix in order to normalise and correct the time window-based feature matrix for the body position change of the user human subject and resulting changes in rib and abdomen displacement transducer function of the second set of transducers from the body position change.

2. The monitoring method as claimed in claim 1, wherein the movement signals from the movement transducers of the second set of transducers are representative of movement in each of an X, Y, and Z dimension, and wherein the movement transducers of the second set of transducers include an accelerometer which is co-located with the rib displacement transducers and the abdomen displacement transducers of the second set of transducers.

3. The monitoring method as claimed in claim 1, wherein the processor also receives blood oxygen level signals representative of a blood oxygen level of the user human subject, and the processor uses the blood oxygen level signals to determine oxygen desaturation events in the user human subject.

4. The monitoring method as claimed in claim 1, wherein the processor:

automatically determines, from the movement signals, if the user human subject has turned so that either the rib or abdomen displacement transducers have reduced function according to the movement signals, automatically identifies sleep cycles per a physical position of the user human subject, and automatically determines end of an apnoea event by detecting the movement signals at the same time as rib displacement signals.

5. The monitoring method as claimed in claim 1, wherein the processor computes sporadic movement characteristics from the use signals.

6. The monitoring method as claimed in claim 1, wherein the processor computes from the use signals characteristics for correlation and covariance between the rib and abdomen displacement signals and the movement signals, and performs secondary measurements of movements to provide breathing features to be extracted and compared.

7. The monitoring method as claimed in claim 1, wherein the processor computes from the use signals characteristics for detection of signal attenuation due to a positioning of the sensor device, wherein the use signals are provided at a frequency in the range of 2 Hz to 200 Hz.

8. The monitoring method as claimed in claim 1, wherein the processor computes from the use signals characteristics for detection of signal attenuation due to positioning of the sensor device, wherein the use signals are provided at a frequency in the range of 2 Hz to 200 Hz, and wherein the time-based windows of said matrix overlap.

9. The monitoring method as claimed in claim 1, wherein the processor: records data from the use signals and performs segmentation into windows of fixed time length, extracts at least one feature for each window of fixed time length, and normalises said features based on a position of the user human subject, in which a threshold is applied according to the second set of transducers and if a signal strength is below the threshold a normalisation factor of zero is applied and populates said time window-based feature matrix.

10. A non-transitory computer readable medium comprising software code for performing the steps of a method of claim 1 when executed by a digital processor.

11. A breathing monitoring system comprising a digital processor linked with transducers mounted on one or more substrates of a sensor device, said transducers including:

rib transducers for sensing rib displacement of a human subject, abdomen transducers for sensing abdomen displacement of the human subject, and movement transducers for sensing movement causing a body position change of the human subject, the rib and abdomen transducers being located on a substrate of the one or more substrates configured to adhere to skin of the human subject;

wherein the digital processor is configured to perform steps of:

in a training phase;

receiving training signals from a first set of the transducers for one or more training human subjects, wherein the first set of the transducers mounted on the one or more substrates of the sensor device are configured to adhere to a torso of the one or more training human subjects, and;

extracting features from the training signals;
performing comparisons with reference diagnostics data to provide a classification model, wherein the reference diagnostics data includes one or any combination of apnoeic event timestamp, apnoeic event type, AHI score, patient position, activity level, sleep stage, wake and sleep time, desaturation events, breathing stoppage events, non-apnoeic breathing disorder events, EEG activity, heart rate, and/or cardiac events; and
training the classification model for characteristics of a user human subject; and in a use phase;
applying a second set of the transducers to the user human subject;
receiving use signals from the second set of the transducers, wherein the second set of the transducers mounted on the one or more substrates of the sensor device are configured to adhere to a torso of the user human subject;
generating breathing event data according to real-time receipt of the use signals from the second set of the transducers, the generating breathing event data including:
using movement signals from movement transducers of the second set of transducers to perform validation of rib displacement signals from rib displacement transducers of the second set of transducers and abdomen displacement signals from abdomen transducers of the second set of transducer, respectively, wherein the using includes:
generating rib and abdomen displacement features according to time-based windows,
determining data for positions of the user human subject after movement and using said positions as start and end events for positional epochs, wherein said data is derived based on the use signals from the second set of transducers,
normalising the rib and abdomen displacement features of the time-based windows within said positional epochs,
developing a normalisation matrix based on said positional epochs, and
applying said normalisation matrix to a time window-based feature matrix in order to normalise and correct the time window-based feature matrix for the body position change of the user human subject and resulting changes in rib and abdomen displacement transducer function of the second set of transducers from the body position change.

12. The monitoring system as claimed in claim 11, wherein the movement signals from the movement transducers of the second set of transducers are representative of movement in each of an X, Y, and Z dimensions, and wherein the movement transducers of the second set of transducers include an accelerometer which is co-located with the rib displacement transducers and the abdomen displacement transducers of the second set of transducers in the sensor device.

13. The monitoring system as claimed in claim 11, wherein the system further comprises a blood oxygen sensor and the processor is adapted to also receive and process blood oxygen level signals representative of a blood oxygen level of the user human subject and to use the blood oxygen level signals to determine oxygen desaturation events in the user human subject.

14. The monitoring system as claimed in claim 11, wherein the processor is configured to automatically determine, from the movement signals, if the user human subject has turned so that either the rib or abdomen displacement transducers have reduced function according to the subject movement signals.

15. The monitoring system as claimed in claim 11, wherein the processor is configured to automatically determine, from the movement signals, if the user human subject has turned so that either the rib or abdomen displacement transducers have reduced function according to the subject movement signal, and wherein the processor is configured to automatically identify sleep cycles per a physical position of the user human subject.

16. The monitoring system as claimed in claim 11, wherein the processor is configured to automatically determine, from the movement signals, if the user human subject has turned so that either the rib or abdomen displacement transducers have reduced function according to the movement signals, and wherein the processor is configured to automatically identify sleep cycles per a physical position of the user human subject, and wherein the processor is configured to automatically determine end of an apnoea event by detecting the movement signals at the same time as rib displacement signals.

17. The monitoring system as claimed in claim 11, wherein the processor is configured to compute sporadic movement characteristics from the use signals.

18. The monitoring system as claimed in claim 11, wherein the processor is configured to:
compute from the use signals characteristics for correlation and covariance between the rib and abdomen displacement signals and the movement signals, and to perform secondary measurements of movements to provide breathing features to be extracted and compared, and to
compute from the use signals characteristics for detection of signal attenuation due to a positioning of the sensor device.

19. The monitoring system as claimed in claim 11, wherein the processor is configured to provide the use signals at a frequency in the range of 2 Hz to 200 Hz, and wherein said time-based windows overlap.

20. The monitoring system as claimed in claim 11, wherein the processor is configured to: record data from the use signals and performs segmentation into windows of fixed time length, extract at least one feature for each window of fixed time length, and normalise said features based on a position of the user human subject, in which a threshold is applied according to the second set of transducers and if a signal strength is below the threshold a normalisation factor of zero is applied and populates said time window-based feature matrix.

* * * * *